United States Patent [19]
Rittner et al.

[11] Patent Number: 5,532,406
[45] Date of Patent: Jul. 2, 1996

[54] PROCESS FOR PREPARING AROMATIC HYDROXYCARBOXYLIC ACIDS

[75] Inventors: Siegbert Rittner, Mörfelden; Hans-Martin Rüffer, Hofheim; Jörg Schmid, Eppstein; Thomas Wisser, Limburg, all of Germany

[73] Assignee: Hoechst Aktiengesellschaft, Germany

[21] Appl. No.: 245,962

[22] Filed: May 19, 1994

[30] Foreign Application Priority Data

May 21, 1993 [DE] Germany ............... 43 16 933.3

[51] Int. Cl.⁶ .................................... C07C 51/15
[52] U.S. Cl. ........................... 562/424; 562/425
[58] Field of Search ................... 562/424–425

[56] References Cited

U.S. PATENT DOCUMENTS

| | | |
|---|---|---|
| 1,593,816 | 7/1926 | Andre . |
| 3,816,521 | 6/1974 | Ueno ............ 562/424 |
| 4,239,913 | 12/1980 | Ueno ............ 562/424 |
| 4,287,357 | 9/1981 | Mueller et al. . |
| 4,329,494 | 5/1982 | Montgomery . |
| 4,966,992 | 10/1990 | Ueno ............ 562/424 |
| 5,072,036 | 12/1991 | Suzuki ............ 562/424 |

FOREIGN PATENT DOCUMENTS

| | | |
|---|---|---|
| 1185264 | 4/1985 | Canada .............. 562/424 |
| 0053824 | 6/1982 | European Pat. Off. . |
| 0081753 | 6/1983 | European Pat. Off. . |
| 0254596 | 1/1988 | European Pat. Off. . |
| 41-5928 | 3/1966 | Japan .............. 562/424 |
| 734622 | 8/1955 | United Kingdom ...... 562/424 |

OTHER PUBLICATIONS

Patent Abstracts of Japan, vol. 6, No. 223 (C–133) (1101), published Nov. 9, 1982.
Patent Abstracts of Japan, vol. 11, No. 273 (C–445) (2720), published Sep. 4, 1987.

*Primary Examiner*—Michael L. Shippen
*Attorney, Agent, or Firm*—Curtis, Morris & Safford

[57] ABSTRACT

A process for preparing aromatic hydroxycarboxylic acids or di-salts thereof by reaction of alkali metal phenolates or naphtholates with carbon dioxide, in the presence or absence of a further alkali metal salt, which comprises introducing the solid phenolate or naphtholate starting materials and, if desired, the alkali metal salt into the reaction mixture batchwise or continuously, separately or together, in the form of a dispersion in an inert organic liquid.

The process of the invention makes possible the preparation of aromatic hydroxycarboxylic acids in good yields and with high chemical selectivity. Additional measures for increasing the selectivity, as are described for the Kolbe-Schmitt reaction in, for example, EP-A 0 053 824, EP-A 0 081 753 and EP-A 0 254 596, can be omitted.

20 Claims, 1 Drawing Sheet

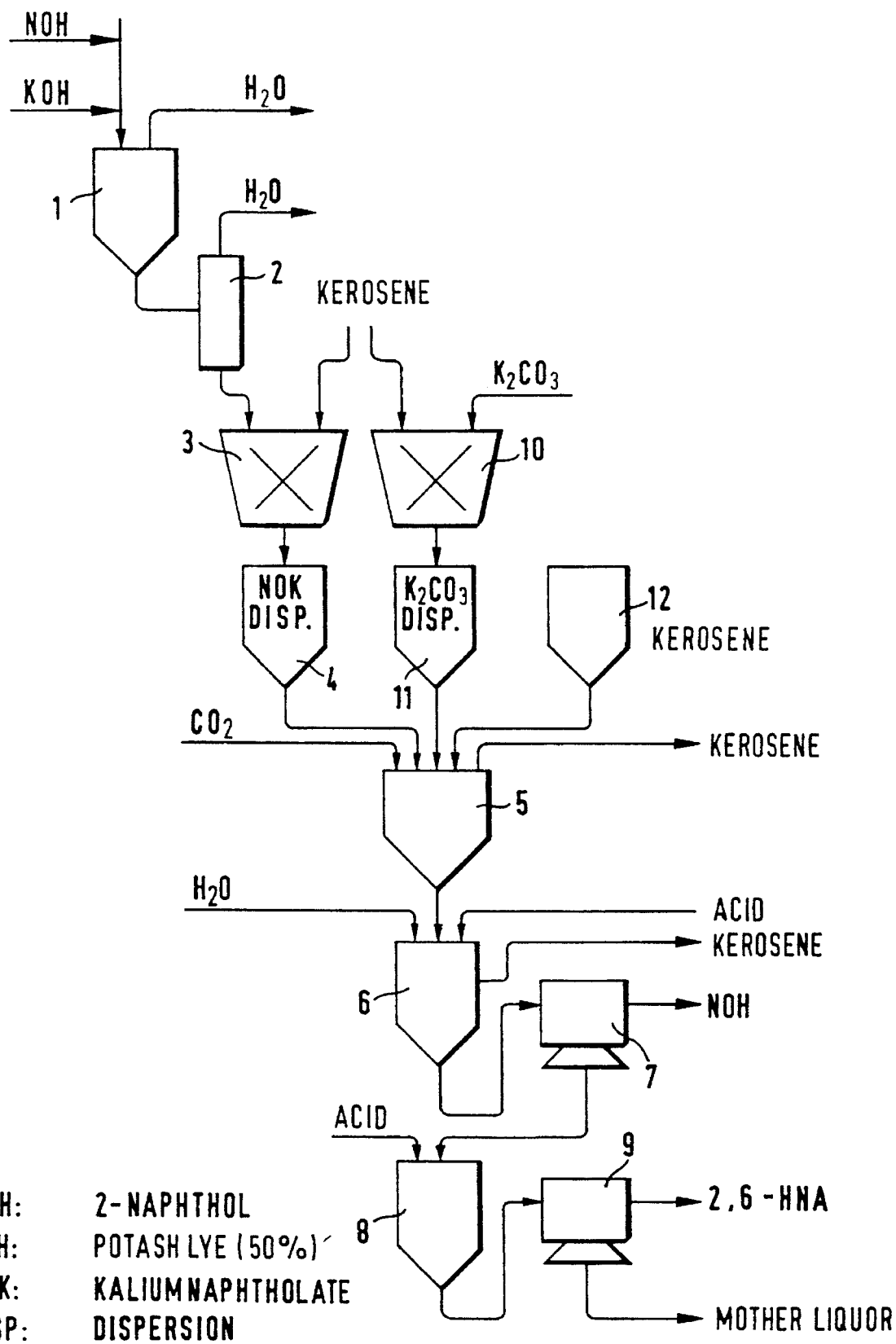

PROCESS FOR PREPARING AROMATIC HYDROXYCARBOXYLIC ACIDS

The invention relates to a process for preparing aromatic hydroxycarboxylic acids by reaction of an alkali metal phenolate (phenoxide) or alkali metal naphtholate (naphthoxide) with $CO_2$.

Aromatic hydroxycarboxylic acids such as 2-hydroxynaphthalene-6-carboxylic acid are important intermediates, for example in the manufacture of dyes, polyesters, pharmaceuticals and textile auxiliaries (see, for example, EP-A 0 292 955 and U.S. Pat. No. 4,393,191).

Industrially, the synthesis of the aromatic hydroxycarboxylic acids is predominantly carried out by a process variant of the so-called Kolbe-Schmitt reaction. In this reaction the alkali metal salt of a phenolate or naphtholate is first prepared in a preliminary stage by reaction of the phenol or naphthol in an aqueous or organic phase with a base such as KOH or $K_2CO_3$. Subsequently the mixture is dewatered as completely as possible and the dry phenolate or naphtholate is reacted with $CO_2$ under pressure at from 200° to 300° C. (see, for example, U.S. Pat. No. 1,593,816, U.S. Pat. No. 4,329,494 and U.S. Pat. No. 4,287,357). However, the process variants described in these disclosures possess some disadvantages, forming significant amounts of decomposition products, such as tars and resins, which, like the isomers often formed in side reactions, can be separated off only with difficulty. In addition, the synthesis by the Kolbe-Schmitt reaction has the disadvantage that for each mole of hydroxycarboxylic acid formed one mole of phenol or naphthol remains unreacted in the reaction mixture, which is why the yield in accordance with the equation 2 mol of alkali metal phenolate or naphtholate
+1 mol of $CO_2 \rightarrow$ 1 mol of di(alkali metal) salt of the hydroxycarboxylic acid +1 mol of phenol or naphthol is in principle limited to 50%. Owing to the tendency of the phenol or naphthol liberated to undergo secondary reactions (formation of tars and resins) with the reaction products already formed, this version of the reaction must result in the abovementioned disadvantages.

Although, for the case of the synthesis of 2-hydroxynaphthalene-6-carboxylic acid, the process methods described in EP-A 0 053 824, EP-A 0 081 753 and EP-A 0 254 596 attempted to improve the reaction procedure and to reduce the formation of the decomposition products by working in inert solvents and continuously removing naphthol from the reaction system by stripping with $CO_2$, there remains the disadvantage of a theoretical yield limited to 50%, even though this can be slightly exceeded in practice by the addition of an alkaline metal salt, for example alkali metal or alkaline earth metal carbonates or hydrogen carbonates, to the reaction batch.

A further problem is posed by the insufficient thermal stability of the alkali metal phenolates and naphtholates which even at the specified reaction temperatures are subject to not inconsiderable decomposition. For the necessary reaction times of between 3 and 10 hours, this means that the batch process methods hitherto customary in practice do not represent the best solution in terms of apparatus, if account is taken of both the high temperature sensitivity and also the reactivity of the phenolate or naphtholate in respect of possible secondary reactions. In the batch process, the starting materials still present in high concentration during the course of the reaction are not converted only to the desired product, but even in the early reaction phase also preferentially undergo secondary reactions which lead to the increased formation of resins and byproducts.

It has now surprisingly been found that alkali metal phenolates and naphtholates and/or alkali metal carbonates form stable flowable and pumpable dispersions with inert organic liquids at room temperature. It has been found that reaction of the solid starting materials in the form of such dispersions can significantly increase the selectivity of the reaction, particularly if the addition to the reaction mixture is extended over the whole course of the reaction.

The invention accordingly provides a process for preparing aromatic hydroxycarboxylic acids or di-salts thereof by reaction of alkali metal phenolates or naphtholates with carbon dioxide, in the presence or absence of a further alkali metal salt, which comprises introducing the solid phenolate or naphtholate starting materials and, if desired, the alkali metal salt into the reaction mixture batchwise or continuously, separately or together, in the form of a dispersion in an inert organic liquid.

For the purposes of the invention, continuously means over the whole course of the reaction, the addition being able to be steady or pulsed, for example via a sluice.

The process of the invention makes possible the preparation of aromatic hydroxycarboxylic acids in good yields and with high chemical selectivity. Additional measures for increasing the selectivity, as are described for the Kolbe-Schmitt reaction in, for example, EP-A 0 053 824, EP-A 0 081 753 and EP-A 0 254 596, can be omitted.

Heat-labile and oxidation-sensitive materials such as the phenolates and naphtholates can be metered in batchwise or continuously at room temperature, and do not have to be, as hitherto, metered in as a melt at high temperatures with the acceptance of decomposition reactions.

The aromatic phenolates or naphtholates preferably used are compounds of the formula (I)

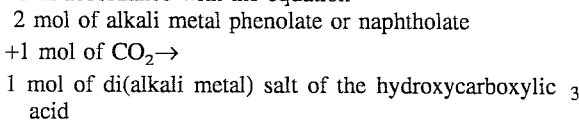

where the symbols and indices have the following meanings:

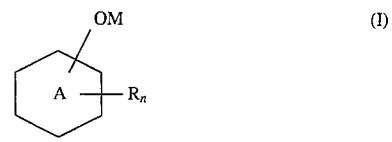

M: Li, Na, K;

R: independently of one another, OM, COOM, F, Cl, Br, I, $NH_2$, $CF_3$, an alkyl group having from 1 to 6 carbon atoms, an alkoxy group having from 1 to 6 carbon atoms;

n: 0, 1, 2, 3, 4.

Preference is given to:

M: Na, K;

R: —OM, —COOM, an alkyl group having from 1 to 6 carbon atoms;

n: 0, 1, 2.

Particular preference is given to:

M: K;

R: COOM, —$CH_3$;

n: 0, 1.

Particularly preferred compounds of the formula (I) are sodium β-naphtholate and potassium β-naphtholate.

The alkali metal phenolates and naphtholates used according to the invention can be prepared by reaction of the corresponding phenols or naphthols with basic alkali metal compounds such as sodium hydroxide and potassium hydroxide.

It is particularly advantageous if in the process of the invention not only the corresponding alkali metal phenolates or naphtholates but also basic salts such as carbonates, hydrogen carbonates, alkylcarboxylates, alkoxides and alkylates are continuously added as a dispersion in an inert organic liquid.

The alkali metal salts used in the process of the invention are preferably alkali metal carbonates and hydrogen carbonates, i.e. $Li_2CO_3$, $LiHCO_3$, $Na_2CO_3$, $NaHCO_3$, $K_2CO_3$, $KHCO_3$, $Rb_2CO_3$, $RbHCO_3$, $Cs_2CO_3$, $CsHCO_3$. Particular preference is given to using $Na_2CO_3$ and $K_2CO_3$, in particular $K_2CO_3$.

The alkali metal salts used according to the invention should preferably contain little moisture, in particular less than 0.5% by weight of water. However, a small amount of moisture is not critical.

The stoichiometric ratio of phenolate or naphtholate to alkali metal salt is generally from 1:0.1 to 1:4, preferably from 1:0.5 to 1:2, particularly preferably 1:1.

The particle size of the solid starting materials used (phenolate or naphtholate and alkali metal salt) preferably lies below 50 μm, particularly preferably below 10 μm, in particular between 0.1 and 10 μm.

Suitable milling devices for the solid starting materials are all comminution machines, for example mills, which can comminute brittle solids to such particle sizes. Particularly good results are achieved if the solids are wet milled directly with the dispersion medium, for example in ball mills.

The dispersion media used for the preparation of the dispersion of the invention are thermally stable liquid materials or mixtures of materials which are inert under the reaction conditions, such as aliphatic, alicyclic or aromatic hydrocarbons from petroleum distillation.

Materials which are particularly suitable are light oil, heavy oil, preferably kerosene, aromatics and their alkyl derivatives such as toluene, xylene, isopropyl- or diisopropylnaphthalene, biphenyl, alkylbiphenyls, triphenyl and alkyltriphenyls, and also aliphatic and aromatic ether compounds and their alkyl derivatives such as diphenyl ether, anisole, dicyclohexyl ether, and mixtures of these. The dispersion media do not interfere with the reaction and can be distilled out of the reactor or subsequent to the reaction can be separated off from the reaction mixture by decantation or distillation. They have the advantage that they can, after removal of possibly dissolved or entrained components such as β-naphthol or water, be used again to produce fresh dispersions.

The metered addition of the phenolates or naphtholates and also of the alkali metal salt can be carried out using one common dispersion or using separate dispersions for the individual materials, the latter possibility offering a greater breadth of variation for the reaction. Suitable means for introduction into the reaction mixture are all metering devices which can convey the dispersions or pastes against the pressure in the reaction vessel, such as piston pumps, diaphragm pumps, extruders and eccentric screw pumps.

The composition of the dispersion can, in terms of weight, lie within wide limits and depends on whether it is to be conveyed as a mobile fluid medium or in pastelike form. A suitable proportion by weight of alkali metal phenolate or naphtholate is from 5 to 70% by weight, preferably from 25 to 60% by weight, in particular between 40 and 55% by weight, based on the total weight of the dispersion. The alkali metal salt can be used within the limits from 5 to 65% by weight, preferably from 20 to 55% by weight, in particular in the range from 25 to 40% by weight, based on the total weight of the dispersion. With solids contents below 25%, it is possible for sedimentation to occur, which can be prevented by either moderate stirring or pumping.

The organic liquids described as dispersion media can also be added to the reaction as additional solvents and diluents, preferably in amounts from 10 to 300% by weight, particularly preferably from 50 to 150% by weight, based on the solid starting materials.

In analogy to the process described in EP-A 0 081 753 for separating off byproducts in the Kolbe-Schmitt synthesis of 2-hydroxynaphthalene-6-carboxylic acid, the dispersion medium and/or an additional diluent can also be used for separating off byproducts.

The process of the invention is carried out in the presence of $CO_2$. The $CO_2$ can be present as a gas atmosphere over the reaction mixture or can alternatively be injected directly onto or into the mixture. At least stoichiometric amounts, based on the phenolate or naphtholate, of $CO_2$ are required for the reaction to proceed successfully.

The process of the invention is conducted at a pressure of from 1 to 50 bar, preferably from 5 to 20 bar and particularly preferably from 8 to 15 bar, the pressure at the reaction temperature being meant.

Technical grade carbon dioxide can be used, i.e. small amounts of extraneous gases such as $N_2$, $CH_4$, $CO$ and $H_2$ are not critical.

The reaction temperature can be varied within wide limits depending on the properties of the starting materials, products and solvents or dispersion media. The reaction is generally carried out at temperatures of from 150° to 400° C., preferably from 150° to 350° C., very particularly preferably from 200° to 350° C. and most preferably from 250° to 350° C.

The duration of the reaction is preferably between 1 and 40 hours.

Different embodiments of apparatus can be used for carrying out the process of the invention; for example the reactor used can be a pressure vessel or kneader which is equipped with an efficient stirring device for thorough mixing and gassing with $CO_2$ and is connected to a feedline for the dispersion. The introduction of the dispersion can be either pulsed by pumping or under pressure, or the dispersion can be metered in continuously.

In a preferred variant of the process of the invention, phenolate or naphtholate and, if desired, the alkali metal salt and dispersion medium are milled and the dispersion thus obtained is introduced continuously or in a pulsed manner into a preheated reactor charged with $CO_2$ and, if desired, with solvent and alkali metal salt. After the reaction is complete, the di-salt of the hydroxycarboxylic acid formed is converted into the free acid and, if desired, is purified by the known methods.

The process of the invention can be operated batchwise, semicontinuously or continuously.

BRIEF DESCRIPTION OF DRAWINGS

FIG. 1 shows a possible variant of apparatus for carrying out the process of the invention.

Procedure using said apparatus for the example of 2-hydroxynaphthalene-6-carboxylic acid:

2-Naphthol is dewatered together with potassium hydroxide solution in the evaporator (1) and freed of residual moisture in the dryer (2). The potassium naphtholate melt formed is subsequently milled with kerosene in the mill (3)

while cooling to give a dispersion and is stored in the tank (4). The reactor (5) is charged with kerosene from the container (12) and the suspension of potassium naphtholate and potassium carbonate (prepared by milling with kerosene in the mill (10) and stored in the tank (11)) is continuously fed into the reactor under $CO_2$ pressure. After the reaction is complete, the reaction melt is taken up in water in the stirred vessel (6) and the kerosene upper phase is decanted off and neutralized with sulfuric acid. The 2-naphthol precipitated is separated off in the centrifuge (7). The acidification and precipitation of the 2-hydroxynaphthalene-6-carboxylic acid is carried out analogously in (8) and (9).

The aromatic hydroxycarboxylic acids prepared according to the process of the invention are important intermediates for the preparation of polyesters, azo dyes and pharmaceuticals.

In particular, 2-hydroxynaphthalene-6-carboxylic acid is not only a useful synthetic building block for dyes, textile auxiliaries and pharmaceuticals (see, for example, EP-A 0 292 955 A), but also an important monomer for the preparation of liquid-crystalline polymers having excellent properties (see, for example, U.S. Pat. No. 4,393,191).

The following examples illustrate the abovedescribed invention. Parts are parts by weight and percentages are percentages by weight, unless indicated otherwise.

EXAMPLES

Example 1

A stainless steel pressure autoclave is charged with 100 parts of kerosene and 38 parts of potassium carbonate and heated to 280° C. It is then pressurized with 10 bar of carbon dioxide. Over the course of 5 hours, 50 parts of potassium β-naphtholate are metered in as a suspension in kerosene via a metering pump, part of the kerosene being distilled off, condensed and transferred out of the reaction vessel at reduced pressure. After cooling, the reaction mixture is taken up in water and the kerosene upper phase is decanted off. After acidification with sulfuric acid to a pH of 7, unreacted β-naphthol can be precipitated and separated off. Further acidification to pH 4 precipitates first the 2-hydroxynaphthalene-6-carboxylic acid and at pH 1 finally the remaining acids. The 2-hydroxynaphthalene-6-carboxylic acid is obtained in a yield of 67% based on potassium β-naphtholate used. In addition, 23% of unreacted β-naphtholate and small amounts of 2-hydroxynaphthalene-3-carboxylic acid and 2-hydroxynaphthalene-3,6-dicarboxylic acid are obtained.

Example 2

A stainless steel pressure autoclave is charged with 50 parts of kerosene and 38 parts of potassium carbonate and heated to 280° C. It is then pressurized with 10 bar of carbon dioxide. Over the course of 5 hours, a mixture of 50 parts of potassium β-naphtholate and 38 parts of potassium carbonate are metered in as a suspension in kerosene via a metering pump, part of the kerosene being distilled off, condensed and transferred out of the reaction vessel at reduced pressure. After the usual workup, the 2-hydroxynaphthalene-6-carboxylic acid is obtained in a yield of 76% based on potassium naphtholate used. In addition, 14% of unreacted β-naphthol and small amounts of 2-hydroxynaphthalene-3-carboxylic acid and 2-hydroxynaphthalene-3,6-dicarboxylic acid are obtained.

Example 3

A stainless steel pressure autoclave is charged with 150 parts of kerosene and 32 parts of sodium carbonate and heated to 240° C. It is then pressurized with 10 bar of carbon dioxide. Over the course of 6 hours, 50 parts of sodium β-naphtholate are metered in as a suspension in kerosene via a metering pump, part of the kerosene being distilled off, condensed and transferred out of the reaction vessel at reduced pressure. After the usual workup, the 2-hydroxynaphthalene-3-carboxylic acid is obtained in a yield of 65% based on sodium β-naphtholate used. In addition, 23% of unreacted β-naphthol and small amounts of 2-hydroxynaphthalene-6-carboxylic acid and 2-hydroxynaphthalene-3,6-dicarboxylic acid are obtained.

Example 4

A stainless steel pressure autoclave is charged with 50 parts of kerosene and heated to 240° C. It is then pressurized with 10 bar of carbon dioxide. Over the course of 8 hours, a mixture of 50 parts of sodium β-naphtholate and 32 parts of sodium carbonate are metered in as a suspension in kerosene via a metering pump, part of the kerosene being distilled off, condensed and transferred out of the reaction vessel at reduced pressure. After the usual workup, the 2-hydroxynaphthalene-3-carboxylic acid is obtained in a yield of 69% based on sodium β-naphtholate used. In addition, 20% of unreacted β-naphthol and small amounts of 2-hydroxynaphthalene-6-carboxylic acid and 2-hydroxynaphthalene-3,6-dicarboxylic acid are obtained.

What is claimed is:

1. A process for preparing aromatic hydroxy carboxylic acids or di-salts thereof by reaction of solid alkali metal phenolate or naphtholate starting materials with carbon dioxide, which comprises introducing the solid phenolate or naphtholate starting materials into a reaction mixture batchwise or continuously, separately or together, in the form of a dispersion in an inert organic liquid.

2. The process as claimed in claim 1, wherein the dispersion is added steadily.

3. The process according to claim 1, wherein the dispersion is added in a pulsed manner.

4. The process as claimed in claim 1,
wherein the phenolate or naphtholate used is a compound of the formula (I)

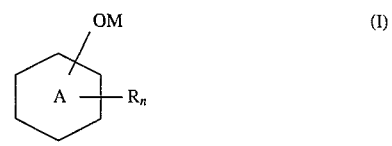

where the symbols and indices have the following meanings:

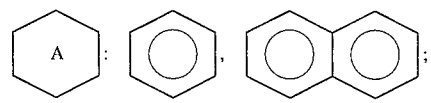

M: Li, Na, K;

R: independently of one another, OM, COOM, F, Cl, Br, I, $NH_2$, $CF_3$, an alkyl group having from 1 to 6 carbon atoms, an alkoxy group having from 1 to 6 carbon atoms;

n: 0, 1, 2, 3, 4.

5. The process as claimed in claim 4, wherein the naphtholate used is potassium β-naphtholate.

6. The process as claimed in claim 1, wherein the inert organic liquid is an aliphatic or aromatic hydrocarbon or ether or a mixture of at least two such compounds.

7. The process as claimed in claim 1, wherein the dispersion comprises from 5 to 70% by weight, based on the total dispersion, of phenolate or naphtholate.

8. The process as claimed in claim 1, wherein the solids used have an average particle size of less than 50 μm.

9. The process as claimed in claim 1, wherein the solid alkali metal phenolate or naphtholate starting materials in the form of a dispersion are introduced to the reaction mixture at room temperature.

10. The process as claimed in claim 1, wherein the aromatic hydroxy carboxylic acid or di-salt is produced with a yield of greater than about 65% based on the starting materials used.

11. The process as claimed in claim 1, wherein the reaction is conducted at a pressure from about 1 to about 50 bar.

12. The process as claimed in claim 1, further comprising the addition of at least one alkali metal salt to the reaction mixture as a dispersion.

13. The process as claimed in claim 1, wherein the alkali metal salt used is potassium carbonate.

14. The process as claimed in claim 12, wherein the dispersion comprises from 5 to 50% by weight, based on the total dispersion, of the alkali metal salt.

15. The process as claimed in claim 12, wherein the alkali metal salt and phenolate or naphtholate are introduced into the reaction mixture in the form of a common dispersion.

16. The process as claimed in claim 12, wherein the alkali metal salt and phenolate or naphtholate are introduced into the reaction mixture in the form of separate dispersions.

17. The process as claimed in claim 12, wherein the at least one alkali metal salt is selected from the group consisting of alkali metal carbonates, hydrogen carbonates and mixtures thereof.

18. The process as claimed in claim 12, wherein at least one alkali metal salt is selected from the group consisting of $Li_2CO_3$, $LiHCO_3$, $Na_2HCO_3$, $K_2CO_3$, $KHCO_3$, $Rb_2CO_3$, $RbHCO_3$, $Cs_2CO_3$, $CsHCO_3$ and mixtures thereof.

19. The process as claimed in claim 12, wherein the at least one alkali metal salt is selected from the group consisting of $Na_2CO_3$, $K_2CO_3$ and mixtures thereof.

20. The process as claimed in claim 12, wherein the at least one alkali metal salt is introduced to the reaction mixture in the same dispersion as the solid alkali metal phenolate or naphtholate starting materials.

* * * * *